United States Patent [19]

Kay et al.

[11] Patent Number: 4,659,848

[45] Date of Patent: Apr. 21, 1987

[54] TITANIUM COMPOSITIONS

[75] Inventors: Peter D. Kay, Hartlepool; Michael C. Girot, Stockton on Tees, both of England

[73] Assignee: Tioxide Group PLC, England

[21] Appl. No.: 754,292

[22] Filed: Jul. 12, 1985

[30] Foreign Application Priority Data

Jul. 20, 1984 [GB] United Kingdom ............... 8418517

[51] Int. Cl.$^4$ ............................................. C07F 7/28
[52] U.S. Cl. ........................................ 556/24; 106/20; 106/23; 106/299; 106/308 Q
[58] Field of Search .......................................... 556/24

[56] References Cited

U.S. PATENT DOCUMENTS

| | | | |
|---|---|---|---|
| 3,275,668 | 9/1966 | Revukas | 556/24 |
| 3,422,126 | 1/1969 | Bauer | 556/24 |
| 4,069,192 | 1/1978 | Monte et al. | 556/24 X |
| 4,087,402 | 5/1978 | Monte et al. | 556/24 X |
| 4,122,062 | 10/1978 | Monte et al. | 556/24 X |
| 4,192,792 | 3/1980 | Sugerman et al. | 556/24 X |

FOREIGN PATENT DOCUMENTS

1525418 9/1978 United Kingdom .

*Primary Examiner*—Helen M. S. Sneed
*Attorney, Agent, or Firm*—Banner, Birch, McKie & Beckett

[57] ABSTRACT

A new organotitanate which is a reaction product of a titanium orthoester and at least a monoalkyl phosphate in which the alkyl group contains up to 6 carbon atoms and in which the total molar ratio P:Ti in the product is less than 2.

The monoalkyl phosphates preferably contain up to 5 carbon atoms in the alkyl group and the organotitanate reaction product can also be prepared from a dialkyl phosphate in addition to the monoalkyl phosphate. Most preferably the alkyl group of the titanium orthoester is either an isopropyl group or a butyl group.

The new reaction products are of use as adhesion promoters in printing inks.

10 Claims, No Drawings

TITANIUM COMPOSITIONS

This invention relates to titanium compositions and particularly to reaction products which are organotitanates.

According to the invention an organotitanate comprises the reaction product of a titanium orthoester and at least a monoalkyl phosphate in which the alkyl group contains up to 6 carbon atoms and in which the total molar ratio P:Ti in the product is less than 2.

The titanates of the invention are the reaction products of a titanium orthoester, and at least a monoalkyl phosphate. If desired a dialkyl phosphate can also be used in addition to the monoalkyl phosphate. Generally speaking the titanium orthoester will have the general formula $Ti(OR)_4$ in which R represents an alkyl group usually containing up to 10 carbon atoms. Preferably R represents an alkyl group containing 3 or 4 carbon atoms and although it is possible that within one molecule of the orthoester different alkyl groups may be present usually they are the same.

The monoalkyl phosphate generally has a formula $(R_1O)PO(OH)_2$ in which $R_1$ represents an alkyl group containing up to 6 carbon atoms, preferably up to 5 carbon atoms. The dialkyl phosphate if used generally has the formula $(R_2O)(R_3O)PO(OH)$ in which $R_2$ and $R_3$ each represents an alkyl group usually containing up to 6 carbon atoms and preferably containing up to 5 carbon atoms. Usually but not necessarily $R_1$, $R_2$ and $R_3$ are identical.

Most preferably the alkyl group of the titanium orthoester is an isopropyl or butyl group.

The organotitanates of the present invention are reaction products of the titanium orthoester in which the total molar ratio P:Ti in the product is less than 2 and preferably less than 1.5.

The alkyl phosphate is added to titanium orthoester or vice-versa to produce the desired reaction product. The reaction can be carried out at room temperature if desired and with stirring and cooling if necessary. The dialkyl phosphate if used can be added separately or with the monoalkyl phosphate.

The new reaction products are of value when used as adhesion promoters in printing inks. A printing ink basically consists of a polymeric binder, a solvent therefor, and usually a pigment and/or a dye. The adhesion promoter is required to promote crosslinking of the polymeric binder and adhesion of the ink to different substrates. The inks which are of particular interest are the flexographic or gravure inks in which the polymeric binder is cross-linkable and is dissolved in an appropriate organic solvent therefor. Typical binders usable in such inks are those based on nitrocellulose or ester type modified celluloses, e.g. cellulose acetate propionate. Often such polymeric binders are employed in mixed form with polyamides, polyurethanes and/or other resins.

The ink usually contains one or more pigments and/or one or more dyes and typical pigments which can be used are the coloured inorganic pigments, white inorganic pigments and coloured organic pigments. Organic dyes can be used to render the ink the appropriate colour and often are used in conjunction with an opacifying white inorganic pigment such as titanium dioxide.

The invention is illustrated in the following Examples:

EXAMPLE 1

To a round bottomed flask equipped with a stirrer, condenser and dropping funnel and containing 284 gms of tetraisopropyl titanate there was slowly added from the funnel 203 gms of a commercial mixture of approximately equi-molar proportions of monoamyl phosphate and diamyl phosphate. The contents were stirred with the flask in a cooling bath until the addition was complete.

An ink was made from the following ingredients in a ball mill:

|  | parts by weight |
| --- | --- |
| Nitrocellulose (Dry wt) | 5.05 |
| Polyurethane resin | 6.72 |
| Rutile $TiO_2$ | 15.54 |
| Dicyclohexyl phthalate | 5.46 |
| Polyethylene wax | 2.00 |
| Isopropanol | 2.16 |
| Industrial methylated spirits | 22.02 |
| Ethyl acetate | 26.17 |
| Toluene | 14.88 |
|  | 100.00 |

To 100 parts by weight of the above ink there was added 1 part by weight of the reaction product by weight of the prepared reaction product.

The so prepared ink was used to prepare and test a printed strip of co-extruded polyethylene/polypropylene and for comparison the ink without added reaction product was used to print an adjacent area of the strip. A sticky tape, (7.6 cm wide) was applied to the printed strip to contact both ink surfaces and pressure applied to ensure good contact.

The tape was then quickly removed from both inks simultaneously and a visual inspection made of the strip. It was apparent that little or no ink containing the titanate was removed whereas virtually all the unmodified ink was removed by the sticky tape.

Samples of co-extrudate printed with both inks were mounted between sheets of aluminium foil and heated to approximately 160° C. for 10 seconds. The heated samples were allowed to cool and the foil removed and inspected. It was clear that less of the modified ink had become transferred to the foil than that of the unmodified ink.

EXAMPLE 2

A titanate was prepared in a manner similar to that described in Example 1 from 340 gms of tetra-n-butyl titanate and 182 gms of an approximately equi-molar mix of monobutyl phosphate and dibutyl phosphate.

The titanate was used to prepare an ink in a similar manner to that of Example 1 and tested similarly.

Again the modified ink exhibited improved adhesion and heat resisting properties.

EXAMPLE 3

A titanate was prepared in apparatus as described in Example 1 from 340 gms of tetra-n-butyl titanate and 154 gms of monobutyl phosphate dissolved in 308 gms of industrial methylated spirits with vigorous stirring.

The titanate solution was used to prepare an ink similar to that of Example 1 except that 1.5 parts by weight of the solution was added and tested similarly.

The modified ink was shown to have similar improved properties to those of Examples 1 and 2.

EXAMPLE 4

A titanate was prepared in apparatus as described in Example 1 from 284 gms of tetraisopropyl titanate and 161 gms of an approximately equi-molar mix of monoisopropyl phosphate and diisopropyl phosphate dissolved in 94 gms of industrial methylated spirits with vigorous stirring.

The titanate obtained was used to prepare an ink in a similar manner to that of Example 1 and tested similarly.

The modified ink was shown to have similar improved properties to those of the modified inks of Examples 1, 2 and 3.

We claim:

1. An organotitanate comprising the reaction product of a titanium orthoester and at least a monoalkyl phosphate in which the alkyl group contains up to 6 carbon atoms and in which the total molar ratio P:Ti in the product is less than 2.

2. An organotitanate according to claim 1 in which the said monoalkyl phosphate has the general formula $(R_1O)PO(OH)_2$ in which $R_1$ represents an alkyl group containing up to 6 carbon atoms.

3. An organotitanate according to claim 2 in which $R_1$ represents an alkyl group containing up to 5 carbon atoms.

4. An organotitanate according to claim 1 in which the said reaction product is of said titanium orthoester, said monoalkyl phosphate and a dialkyl phosphate.

5. An organotitanate according to claim 4 in which the said dialkyl phosphate has the general formula $(R_2O)(R_3O)PO(OH)$ in which $R_2$ and $R_3$ each represents an alkyl group containing up to 6 carbon atoms.

6. An organotitanate according to claim 5 in which $R_2$ and $R_3$ each represents an alkyl group containing up to 5 carbon atoms.

7. An organotitanate according to claim 5 in which $R_1$, $R_2$ and $R_3$ each represent identical alkyl groups.

8. An organotitanate according to claim 1 in which the said titanium orthoester has the general formula $Ti(OR)_4$ in which R represents an alkyl group containing up to 10 carbon atoms.

9. An organotitanate according to claim 8 in which R represents an alkyl group containing 3 or 4 carbon atoms.

10. An organotitanate according to any one of the preceding claims in which the total molar ratio P:Ti in the product is less than 1.5.

* * * * *